(12) United States Patent
Banerjee et al.

(10) Patent No.: US 10,556,942 B2
(45) Date of Patent: Feb. 11, 2020

(54) PROCESS FOR THE PURIFICATION OF TNFR:FC FUSION PROTEIN

(71) Applicant: LUPIN LIMITED, Mumbai (IN)

(72) Inventors: Abir Banerjee, Pune (IN);
Chandranath Ganapathy, Pune (IN);
Sorab Rustom Mody, Pune (IN);
Ashok Mishra, Pune (IN)

(73) Assignee: LUPIN LIMITED, Mumbai (IN)

( * ) Notice: Subject to any disclaimer, the term of this patent is extended or adjusted under 35 U.S.C. 154(b) by 160 days.

(21) Appl. No.: 15/318,489

(22) PCT Filed: Jun. 13, 2015

(86) PCT No.: PCT/IB2015/054494
§ 371 (c)(1),
(2) Date: Dec. 13, 2016

(87) PCT Pub. No.: WO2015/189832
PCT Pub. Date: Dec. 17, 2015

(65) Prior Publication Data
US 2017/0152298 A1 Jun. 1, 2017

(30) Foreign Application Priority Data
Jun. 13, 2014 (IN) .......... 1919/MUM/2014

(51) Int. Cl.
| | | |
|---|---|---|
| *C07K 16/22* | (2006.01) |
| *C07K 1/18* | (2006.01) |
| *C07K 14/705* | (2006.01) |
| *B01D 15/12* | (2006.01) |
| *B01D 15/20* | (2006.01) |
| *B01D 15/30* | (2006.01) |
| *B01D 15/36* | (2006.01) |
| *B01D 15/38* | (2006.01) |
| *B01D 15/42* | (2006.01) |

(52) U.S. Cl.
CPC ........ *C07K 14/70578* (2013.01); *B01D 15/12* (2013.01); *B01D 15/203* (2013.01); *B01D 15/30* (2013.01); *B01D 15/363* (2013.01); *B01D 15/3809* (2013.01); *B01D 15/3847* (2013.01); *B01D 15/424* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 7,294,481 | B1 | 11/2007 | Fung | |
| 2014/0187751 | A1* | 7/2014 | Nti-Gyabaah | C07K 1/36 530/387.3 |
| 2015/0290325 | A1* | 10/2015 | Kashi | C07K 14/7151 424/134.1 |
| 2019/0085021 | A1* | 3/2019 | Trejo | C07K 14/7151 |

FOREIGN PATENT DOCUMENTS

| | | |
|---|---|---|
| CN | 102911250 | 2/2013 |
| EP | 2729482 | 5/2014 |
| WO | 2004076485 | 9/2004 |
| WO | 2009053360 | 4/2009 |
| WO | 2010056550 | 5/2010 |
| WO | 20120176158 | 12/2012 |
| WO | 20130176754 | 11/2013 |
| WO | 2014043103 | 3/2014 |
| WO | 2014078627 | 5/2014 |

* cited by examiner

*Primary Examiner* — Michael D Pak
(74) *Attorney, Agent, or Firm* — Duane Morris LLP; J. Rodman Steele, Jr.; Gregory M. Lefkowitz (57) ABSTRACT

The present invention relates to the purification of TNFR:Fc fusion protein. More specifically related to process of purification of TNFR:Fc fusion protein wherein the HCP is reduced. The present invention is directed to the use of mixed-mode chromatography and/or affinity chromatography to produce TNFR:Fc fusion protein which is substantially free of at least one of the protein degrading enzyme present in HCP.

20 Claims, 4 Drawing Sheets

PROCESS FOR THE PURIFICATION OF TNFR:FC FUSION PROTEIN

CROSS-REFERENCE TO RELATED APPLICATIONS

This application is a § 371 national stage entry of International Application No. PCT/IB2015/054494, filed Jun. 13, 2015, which claims priority to Indian Patent Application No. 1919/MUM/2014, filed Jun. 13, 2014, the entire contents of which are incorporated herein by reference.

FIELD OF THE INVENTION

The present invention relates to the purification of TNFR:Fc fusion protein. More specifically purification of TNFR:Fc fusion protein wherein the HCP is reduced. The present invention is directed to the use of mixed-mode chromatography and/or affinity chromatography to produce TNFR:Fc fusion protein which is substantially free of at least one of the protein degrading enzyme present in HCP.

BACKGROUND OF THE INVENTION

Proteins are important in biopharmaceuticals as they are widely used to cure a number of diseases including diabetes (e.g. Insulin), cancers (e.g. Interferon, monoclonal antibodies), heart attacks, strokes, cystic fibrosis (e.g. Enzymes, Blood factors), inflammation diseases (e.g. Tumor Necrosis Factors), anemia (e.g. Erythropoietin), hemophilia (e.g. Blood clotting factors), etc. One of the important challenges is the development of efficient and competent process for the large scale purification of these proteins. Numerous processes are available for the large scale purification of the Protein-of-interest from the harvest cell culture fluid (HCCF), but still some impurities remain with the purified Protein-of-interest which can prove to be detrimental to the long term stability as well as quality of the Protein-of-interest. The Protein-of-interest is purified from the HCCF using a series of chromatographic and Ultrafiltration/Diafiltration techniques.

Although a lot of processes have been developed to purify TNFR:Fc fusion proteins from the HCCF, but due to variability in the cell expression system, it has been observed that general purification processes often fail to adequately purify the Protein-of-interest from the process related impurities. The Protein-of-interest produced by the host cells during cell culture or fermentation has to be purified from host cell-derived proteins (HCP), host-cell DNA, process additives, adventitious agents, toxins and certain product-related substances. These impurities are undesirable in the purified Protein-of-interest and their levels need to be kept within the acceptable levels to render the product safe for human therapeutic use (Wang et. al. 2009 Jun. 15 *Biotechnol Bioengineering* 103(3):446-58).

Tumour necrosis factor (TNF) is a potent cytokine and elicits a broad spectrum of biologic responses, which are mediated by binding to a cell surface receptor. It is involved in pathogenesis of many inflammatory disorders like rheumatoid arthritis, psoriatic arthritis, SLE, Crohn's disease etc. Hohmann et. al. (Hohmann et. al. 1989 *J Biol Chem.* 25, 14927-34). Direct inhibition of TNF-alpha by the biological agents has produced significant advances in rheumatoid arthritis treatment and has validated the extra-cellular inhibition of this pro-inflammatory cytokine as an effective therapy. Recombinant TNFR:Fc fusion proteins bind to the cytokine TNF and block the activity of TNF. Examples of TNF-inhibitors include TNFR:Fc fusion protein (Etanercept) and anti-TNF monoclonal antibodies (Adalimumab, Infliximab, Golimumab and Certolizumabpegol).

Etanercept is a dimeric fusion protein consisting of an extra-cellular ligand-binding portion of the human 75 kilo Dalton (p75) tumor necrosis factor receptor (TNFR, type II) linked to the Fc portion of human IgG1. The Fc component of Etanercept consists of the $CH_2$ domain, the $CH_3$ domain and hinge region, whereas the $CH_1$ domain is absent (U.S. Pat. No. 7,648,702). It is produced through recombinant DNA technology in Chinese hamster ovary mammalian cells. It consists of 934 amino acids, and has an apparent molecular weight of approximately 130 kilo Dalton. Due to its unique structure, Etanercept binds more efficiently to TNF alpha than its endogenous receptor (Gofeeet et. al. 2003 *J Am Acad Dermatol.* 49, S105-111, Strober 2005 *Semin Cutan Med Surg.* 24; 28-36).

U.S. Pat. No. 7,294,481 discloses purification of TNFR:Fc protein by protein A chromatography followed by hydrophobic interaction chromatography.

EP2729482A1 discloses purification of fusion proteins by protein A chromatography, followed by cation exchange chromatography followed by anion exchange chromatography.

WO2004076485 teaches purification of antibodies by protein A chromatography followed by anion exchange chromatography followed by cation exchange chromatography.

WO2013176754 discloses a method for reducing at least one process-related impurity and/or product-related substance from the Protein-of-interest by hydrophobic interaction chromatography (HIC) in flow through mode.

SUMMARY OF THE INVENTION

In an embodiment, the invention is related to a process of TNFR:Fc fusion proteins purification by performing Mixed-mode chromatography in the flow through mode.

In another embodiment, the invention is related to a process for reducing HCP from TNFR:Fc fusion proteins by performing Mixed-mode chromatography in the flow through mode.

In another embodiment, the invention is related to a process for reducing HCP by chromatographic processes comprising of protein A chromatography and mixed mode chromatography.

In yet another embodiment, the invention is related to the method of reducing HCP from TNFR:Fc fusion protein by performing protein A chromatography, which is followed by hydrophobic interaction chromatography (HIC), which is followed by anion exchange chromatography which is followed by Mixed-mode chromatography.

In yet embodiment, the invention is related to a process for reducing HCP, aggregates, and misfolds to give substantially pure (99% pure TNFR:Fcfusion protein by Size Exclusion-High Pressure Liquid Chromatography (SE-HPLC) and >80% pure TNFR:Fc fusion protein by Hydrophobic Interaction (HI)-HPLC.

In an embodiment the invention is related to the use of mixed-mode chromatography to produce TNFR:Fc fusion protein which is substantially free of at least one of the protein degrading enzyme present in HCP.

In an embodiment the invention is related to the process for purifying the protein from the protein mixture comprising TNFR:Fc fusion protein and HCP impurities, the said process comprising:

a) obtaining protein mixture from the suitable mammalian expression system comprising TNFR:Fc fusion protein and host cell protein (HCP) impurities containing at least one protein degrading enzyme;

b) applying the protein mixture to affinity chromatography column;

c) eluting the TNFR:Fc fusion protein from affinity chromatography column wherein the eluted TNFR:Fc fusion protein is present in second protein mixture contains reduced amount of HCP impurity;

d) applying the second protein mixture to mixed-mode chromatography column;

e) eluting the TNFR:Fc fusion protein from a mixed-mode chromatography column wherein the eluted TNFR:Fc fusion protein is substantially free of HCP impurities containing at least one of the protein degrading enzyme.

In another embodiment the invention is related to the process for purifying the TNFR:Fc fusion protein from the protein mixture comprising TNFR:Fc fusion protein and at least one HCP impurity containing protein degrading enzyme, the said process comprising:

a) obtaining protein mixture from the suitable mammalian expression system comprising TNFR:Fc fusion protein and host cell protein (HCP) impurities containing at least one protein degrading enzyme;

b) applying the protein mixture to affinity chromatography column;

c) eluting the TNFR:Fc fusion protein from affinity chromatography column wherein the eluted TNFR:Fc fusion protein is present in second protein mixture contains reduced amount of HCP impurity;

d) applying the second protein mixture to Hydrophobic interaction chromatography column;

e) eluting the TNFR:Fc fusion protein from a Hydrophobic interaction chromatography column wherein the eluted protein of interest is present in third protein mixture containing reduced amount of HCP impurity;

f) applying the third protein mixture to mixed-mode chromatography column;

g) eluting the TNFR:Fc fusion protein from a mixed-mode chromatography column wherein the eluted protein of interest is substantially free of HCP impurity containing at least one of the protein degrading enzyme.

In another embodiment the invention is related to the process for purifying the protein from the protein mixture comprising TNFR:Fc fusion protein and at least one HCP impurity containing protein degrading enzyme, the said process comprising:

a) obtaining protein mixture from the suitable mammalian expression system comprising TNFR:Fc fusion protein and host cell protein (HCP) impurities containing at least one protein degrading enzyme;

b) applying the protein mixture to affinity chromatography column;

c) eluting the TNFR:Fc fusion protein from affinity chromatography column wherein the eluted TNFR:Fc fusion protein is present in second protein mixture contains reduced amount of HCP impurity;

d) applying the second protein mixture to Hydrophobic interaction chromatography column;

e) eluting the TNFR:Fc fusion protein from a Hydrophobic interaction chromatography column wherein the eluted TNFR:Fc fusion protein is present in third protein mixture contains reduced amount of HCP impurity;

f) applying the third protein mixture to anion exchange chromatography column;

g) eluting the TNFR:Fc fusion protein from a anion exchange chromatography column wherein the eluted protein of interest is present in fourth protein mixture contains reduced amount of HCP impurity;

h) applying the fourth protein mixture to mixed-mode chromatography column;

i) eluting the TNFR:Fc fusion protein from a mixed-mode chromatography column wherein the eluted TNFR:Fc fusion protein is substantially free of HCP impurity containing at least one of the protein degrading enzyme.

In another embodiment the invention is related to the process for purifying the TNFR:Fc fusion protein from the protein mixture by using mixed-mode chromatography column which can be performed at any step after affinity chromatography column.

In another embodiment the invention is related to the process for purifying the TNFR:Fc fusion protein from the protein mixture comprising TNFR:Fc fusion protein and at HCP impurities, the said process comprising:

a) obtaining protein mixture from the suitable mammalian expression system comprising fusion and host cell protein (HCP) impurities containing at least one protein degrading enzyme;

b) applying the protein mixture to affinity chromatography column;

c) applying more than one wash to affinity chromatography column;

d) eluting the TNFR:Fc fusion protein from affinity chromatography column wherein the eluted TNFR:Fc fusion protein contains reduced amount of HCP impurities comparatively performed the said process without applying more than one wash to affinity chromatography column.

In yet another embodiment the invention substantially reduced the HCP impurities containing at least one protein degrading enzyme by at least 90% preferably by at least 99% and more preferably reduced to the extent to meet acceptable limit.

In yet another embodiment the invention substantially reduced the HCP impurities containing at least one protein degrading enzyme and stabilize the TNFR:Fc fusion protein by at least two weeks, preferably by at least one month, more preferably by at least 6 month and most preferably by at least one year.

In an embodiment, the invention is related to a process of TNFR:Fc fusion proteins purification by performing Mixed-mode chromatography in the flow through mode.

The details of one or more embodiments of the invention set forth below are illustrative in nature only and not intended to limit the scope of the invention. Other features, objects and advantages of the inventions will be apparent from the description.

DETAILED DESCRIPTION OF THE INVENTION

The invention relates to the process of purifying TNFR:Fc fusion protein from HCCF obtaining from a fed-batch and/or perfusion technology.

The invention is related to the use of mixed-mode chromatography to produce TNFR:Fc fusion protein which is substantially free of at least one of the protein degrading enzyme present in HCP.

The invention relates to the process of reducing impurities, especially HCP, from the Protein-of-interest by intermediate chromatographic processes comprising of protein A and Mixed-mode chromatography. The HCP reduced by 90%, more specifically the HCP is reduced by 99%. Preferably HCP is reduced to the extent to meet acceptable limit.

HCP can cause an immune response in patients at levels as low as 100 parts per million (ppm). HCPs are commonly present in small quantities in the drug substance and the drug product as they are not fully eliminated by conventional methods of purification. Much effort and cost is expended by industry to remove HCPs as much as possible.

As used herein, the terms "host cell proteins (HCP)" comprises of protein degrading enzyme which is proteases and other non-target protein-related, proteinaous impurities derived from host cells. HCP clearance is of even more significance when one or more of the HCP is a protease as it can hydrolyze (degrade) the Protein-of-interest. Presence of protease, even at a very low level, can compromise the long-term stability of the Protein-of-interest. In addition to protein degrading enzyme, HCP contains impurities which includes but not limited to aggregates, misfolded protein and fragments.

Any Protein A chromatography resin, when used as a capture step for TNFR:Fc fusion proteins and other monoclonal antibodies, can clear a large proportion of the impurities from the HCCF, but some amount of HCPs, inclusive of one or more proteases such as matrix metalloprotease (preferably gelatinases) can still co-elute with the Protein-of-interest due to non-specific binding to the protein A resin. Combinations of different chromatography steps further helps to remove trace amounts of protease, which are still present after protein A chromatography.

As used herein, the term "bind-elute mode" refers to a mode of purification by chromatography, wherein the Protein-of-interest when loaded on the column is bound to the chromatographic resin and is subsequently eluted with an elution buffer.

As used herein, the term "flow-through mode" refers to a mode of purification by chromatography, wherein the high molecular weight impurities, HCP and endotoxins are bound to the chromatographic resin when loaded and the Protein-of-interest comes out in the flow though.

As used herein, the term "fusion proteins" include but are not limited to etanercept, abatacept, alefacept, rilonacept, belatacept, aflibercept.

As used herein, the term "TNFR" is a biologically active glycoprotein which comprises full or in part the extracellular, soluble fragment of a protein belonging to the TNF receptor family. Some examples of TNF receptor family are Tumor Necrosis Factor Receptor I (TNFRI), Tumor Necrosis Factor Receptor II (TNFRII), OX40 Antigen, CD40L Receptor, FASL Receptor. The TNFR1 consists of an extracellular ligand binding portion of human 55 kilo Dalton (p55) and The TNFRII consists of an extra-cellular ligand binding portion of human 75 kilo Dalton (p75).

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The phrase "viral reduction/inactivation", as used herein, is intended to refer to a decrease in the number of viral particles in a particular sample ("reduction"), as well as a decrease in the activity, for example, but not limited to, the infectivity or ability to replicate, of viral particles in a particular sample ("inactivation"). Such decreases in the number and/or activity of viral particles can be on the order of about 1% to about 99%, preferably of about 20% to about 99%, more preferably of about 30% to about 99%, more preferably of about 40% to about 99%, even more preferably of about 50% to about 99%, even more preferably of about 60% to about 99%, yet more preferably of about 70% to about 99%, yet more preferably of about 80% to 99%, and yet more preferably of about 90% to about 99%.

The term "aggregates" used herein means agglomeration or oligomerization of two or more individual molecules, including but not limiting to, protein dimers, trimers, tetramers, oligomers and other high molecular weight species. Protein aggregates can be soluble or insoluble.

The term "protein degrading enzyme" used herein means the impurity derived from the host cell protein and that degrade the protein of interest. "Protein degrading enzyme" includes but not limited to proteases, matrix metalloprotease, gelatinases.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate {e.g., a harvested cell culture fluid ("HCCF") comprising a protein of interest such as a TNFR:Fc fusion protein expressed in a CHO cell). The amount of CHOP present in a mixture comprising a protein of interest provides a measure of the degree of purity for the protein of interest. HCP or CHOP includes, but is not limited to, a protein of interest expressed by the host cell, such as a CHO host cell. Typically, the amount of CHOP in a protein mixture is expressed in parts per million relative to the amount of the protein of interest in the mixture.

The term "linear gradient" is used here to refer to conditions in which pH and/or conductivity is either increased or decreased gradually using at least two buffers wherein the buffers are different in terms of pH or conductivity or both.

The term "gradient elution" is used herein to refer generally to conditions in which pH and/or conductivity is either increased or decreased using at least two buffers wherein the buffers are different in terms of pH or conductivity or both.

The terms "purifying," "separating," or "isolating," as used interchangeably herein, refer to increasing the degree of purity of a polypeptide or protein of interest or a target protein from a protein mixture comprising the polypeptide and one or more impurities or contaminants including at least one of the protein degrading enzyme. Typically, the degree of purity of the target protein is increased by removing (completely or partially) at least one impurity from the composition.

A "purification step" or "unit operation" may be part of an overall purification process resulting in a "homogeneous" composition or sample, which is used herein to refer to a composition or sample comprising less than 1000 ppm HCP in a composition comprising the protein of interest, alternatively less than 900 ppm, less than 800 ppm, less than 700 ppm, less than 600 ppm. The terms "purifying," "separating," or "isolating," as used interchangeably herein, refer to increasing the degree of purity of a polypeptide or protein of interest or a target protein from a composition or sample comprising the polypeptide and one or more impurities or contaminants.

Typically, the degree of purity of the target protein is increased by removing (completely or partially) at least one impurity from the composition. The degree of purity of the target protein is at least 50%, 60%, 70%, 80%, 90%, 95% or 99%.

The term "protein mixture" used herein refers to elute composition obtaining from one or more chromatographic steps employed in the present invention. The term "protein mixture" further define in the present invention as "first protein mixture", "Second protein mixture", "Third protein mixture", "Fourth protein mixture", "Fifth protein mixture" according to chromatographic column used and to the extent of impurities such as incomplete Fc-containing protein fragments, aggregates and host cell proteins (HCPs) and protein degrading enzyme that may be present in the protein mixture. However, the term "first protein mixture", "Second protein mixture", "Third protein mixture", "Fourth protein mixture", "Fifth protein mixture" are interchangeable according to shifting or removing of the chromatographic column employed in purification strategies.

In an embodiment, the TNFR:Fc fusion protein is Etanercept. Etanercept isoelectric point (pI) value is selected from about 4.8 to 5.2.

In certain embodiment, the harvest cell culture fluid (HCCF) is obtaining from the suitable mammalian system, preferably CHO cell culture. Clarification of HCCF can be performed with centrifugation and/or filtration techniques. The 0.2 micron filter is used to produce clarified harvest cell culture fluid (HCCF) which can be further purified by chromatography techniques described in the present invention.

In certain embodiment, the invention is related to the process of purifying the TNFR:Fc fusion protein by employing mixed-mode chromatography. In specific embodiment, the process herein employs at least one affinity chromatography step, preferably protein A chromatography and at least one mixed-mode chromatographic step.

In certain embodiment, the process herein employs at least one affinity chromatography step and at least one mixed-mode chromatographic step and at least one or more additional chromatography steps. The additional chromatography steps can be selected from ion exchange, preferably anion exchange and hydrophobic interaction chromatography (HIC).

In an embodiment the affinity chromatography column is selected from Protein A resin, Protein G resin, preferably Protein A resin. Protein A column chromatography resin is selected from Mab Select Sure LX, MabSelectSuRe, MabSelectXtra, ProSep Ultra Plus, Toyopearl AF-rProtein A HC-650.

In one embodiment, the affinity chromatography step comprises clarified harvest cell culture fluid (HCCF) which is obtaining from suitable mammalian expression system. The pH of HCCF is adjusted to pH selected from about pH 8 to about pH 9, preferably pH 8.5 with 2 M Tris base just before loading onto the affinity column. The protein A column is equilibrated with a suitable buffer prior to sample loading. The suitable buffer is selected from Tris-Cl buffer, HEPES, Triethanolamine, Borate, Glycine-NaOH, preferably Tris-Cl buffer at pH selected from about pH 8 to about pH 9, preferably pH 8.5 and conductivity is selected from about from 10 mS/cm to about 30 mS/cm, preferably about 18 mS/cm. The concentration of the buffer are selected from about 30 mM to about 60 Tris-Cl buffer, preferably 50 mM tris-Cl containing additives about 120 mM to about 150 mM NaCl, preferably 150 mM NaCl and about 2 mM to about 6 mM EDTA, preferably 5 mM EDTA. The protein A column is equilibrated with a suitable buffer for at least one column volumes, preferably for two column volumes. The pH adjusted protein mixture comprises protein of interest and HCP containing at least one protein degrading enzyme is loaded onto Protein A column. The flow rate can be selected from at about 50 cm/hr to at about 300 cm/hr, preferably 100 cm/hr. Following the loading of the Protein A column, the column can be washed one or multiple times by using the equilibrating buffer or by employing different buffers. The Protein A column is first washed with the equilibration buffer for at least 2 column volumes. This wash can optionally be followed by one or more wash. In preferred embodiment, the Protein A column is first washed with the equilibration buffer for at least 2 column volumes and then followed by an intermediate wash buffer referred as wash buffer A which comprises at least one of the following additives urea, tween 80 and isopropanol, NaCl, EDTA in suitable buffer selected from Tris-Cl, HEPES, Triethanolamine, Borate, Glycine-NaOH, preferably Tris-Cl at pH selected from about pH 8 to about pH 9, preferably pH 8.5, conductivity is selected from about from 50 mS/cm to about 75 mS/cm, preferably about 65 mS/cm for at least more than one column volumes, preferably 3 column volumes, more preferably 6 column volumes. The concentration of the wash buffer A is selected from about 30 mM to about 60 Tris buffer, preferably 50 mM Tris buffer containing about 1M to about 2 M urea, preferably 1.5M urea, about 1.5% tween 80, about 7.5% isopropanol, about 0.5 M to about 2 M NaCl, preferably 1M NaCl and about 2 mM to about 6 mM EDTA, preferably 5 mM EDTA.

Following the wash buffer A, the Protein A column is further washed by an intermediate wash buffer referred as wash buffer B which comprises trisodium citrate dihydrate, Acetate, Glycine-HCl, preferably trisodium citrate dehydrate at pH selected from about pH 4 to about pH 5, preferably pH 4.5, conductivity is selected from about from 8 mS/cm to about 25 mS/cm, preferably about 12 mS/cm for at least one column volume. The concentration of the wash buffer B is selected from about 30 mM to about 60 trisodium citrate dihydrate, preferably 50 mM. Following the wash buffer B, the Protein A column is further washed by an intermediate wash buffer referred as wash buffer C which comprises 90% of the wash buffer B and 10% of the elution buffer and wash buffer C pH is about 4.

The Protein A column can then be eluted using an appropriate suitable buffer. The elution buffer can be one or mixture of more than one buffer. The protein is eluted by a combination of linear gradient and step gradient in order to remove oxidized impurities. The linear gradient is achieved by using elution buffer selected from pH about 2 to 3.5 and wash buffer is selected from pH about 4 to 5 in suitable ration.

The linear gradient is achieved by using elution buffer from about from 0 to 100%, preferably from 10 to 90% with elution buffer for at least more than one column volume, preferably linear gradient is achieved by using elution buffer about 10% with 90% wash buffer B for at least more than one column volume, preferably more than 3 column volume, more preferably 6 column volume. Step gradient is achieved by using elution buffer comprising trisodium citrate dihydrate at pH selected from about pH 2 to about pH 3.5, preferably pH 3, conductivity is selected from about from 5 mS/cm to about 15 mS/cm, preferably about 12 mS/cm. The concentration of the trisodium citrate dihydrate is selected from about 30 mM to about 60 mM trisodium citrate dihydrate, preferably 50 mM. The collected fraction is a second protein mixture and optionally can be subjected to low pH treatment.

In certain embodiment the invention can be performed with only Protein A chromatography column. However the purity of the eluted TNFR:Fc fusion protein depends on the one or more of washing steps and removing or reducing the washing steps increase the concentration of protein degrading enzyme respectively.

In another embodiment the invention is related to the process for purifying the TNFR:Fc fusion protein from the protein mixture comprising TNFR:Fc fusion protein and at HCP impurities the said process comprising:

a) obtaining protein mixture from the suitable mammalian expression system comprising fusion and host cell protein (HCP) impurities containing at least one protein degrading enzyme;

b) applying the protein mixture to affinity chromatography column;

c) applying more than one wash to affinity chromatography column;

c) eluting the TNFR:Fc fusion protein from affinity chromatography column wherein the eluted TNFR:Fc fusion protein contains reduced amount of HCP impurities comparatively performed the said process without applying more than one wash to affinity chromatography column.

In embodiment, the viral inactivation can be performed at low pH treatment. The pH of the elute obtained from affinity chromatography (second protein mixture) is selected from about pH 2 to about pH 5, preferably pH 3.5. The pH can be adjusted by suitable acids including, but not limited to, citric acid, acetic acid, caprylic acid, or other suitable acids. If the pH is less than 3.5, it is adjusted to 3.5 with 2 M Tris base. After, the suitable pH 3.5 is achieved then the protein mixture is incubated for at least for 10 minute, preferably 45 minutes at room temperature. Post viral inactivation, the pH of the solution is brought to about 6.5 with 2 M Tris base. Artificial pool is prepared with the low pH treated fractions and impurity profile, preferably oxidized species is checked by protein A HPLC.

In certain embodiment, the present invention also embodies the use of Hydrophobic Interaction Chromatography (HIC) process for purifying the TNFR:Fc fusion protein from mixture comprising protein of interest and HCP containing at least one protein degrading enzyme.

The second protein mixture obtained from affinity chromatography column and optionally after treating low pH treatment can be subjected to a hydrophobic interaction chromatography column and the eluate obtained from HIC column can be referred as third protein mixture which has reduced level of HCP and protein degrading enzymes.

In one embodiment, the hydrophobic interaction chromatography is selected from Butyl Toyopearl 650 M resin, Toyopearl Phenyl-650, Butyl Sepharose 6 Fast Flow, Phenyl Sepharose 6 Fast Flow (High Sub).

In an embodiment the second protein mixture obtained from affinity chromatography column and optionally after treating with low pH treatment is subjected to a hydrophobic interaction chromatography column. HIC is performed in bind-elute mode. Prior to loading, suitable high salt buffer is gradually added in to second protein mixture till the conductivity reaches to about from 40 mS/cm to about 70 mS/cm, preferably about 50 mS/cm. The suitable high salt buffer is selected from at least one or any combination of the salts selected from disodium hydrogen phosphate anhydrous, Trisodium citrate dihydrate, Histidine-HCl, Imidazole, bis-tris, maleate, preferably disodium hydrogen phosphate anhydrous, Trisodium citrate dehydrate at pH selected from about pH 6 to about pH 7, preferably pH 6.5, conductivity is selected from about from 50 mS/cm to about 80 mS/cm, preferably about 65 mS/cm. The concentration of the high salt buffer is selected from about 0.01 M to about 1M, preferably 0.05 M disodium hydrogen phosphate anhydrous, about 0.1 M to about 2M, preferably 0.8 M Trisodium citrate dihydrate. The HIC column is equilibrated with a suitable buffer prior to sample loading. The suitable equilibration buffers are selected from high salt buffer diluted with water for injection (WFI) till the conductivity reaches to about from 40 mS/cm to about 70 mS/cm, preferably about 50 mS/cm. The second protein mixture is loaded onto the HIC column. The flow rate can be selected from at about 50 cm/hr to at about 300 cm/hr, preferably 150 cm/hr.

Following the loading of the HIC column, the column can be washed one or multiple times by using the equilibrating buffer or by employing different buffers. The HIC column is washed with the equilibration buffer for at least one column volumes, preferably 1.5 column volumes. This wash can optionally be followed by one or more wash. In preferred embodiment, HIC column is washed with the equilibration buffer for at least one column volumes, preferably 1.5 column volumes and then followed by an second wash buffer which comprises at least about 10% to 25% of disodium hydrogen phosphate anhydrous and pH is selected from about pH 6 to about pH 7, preferably pH 6.5, conductivity is selected from about from 5 mS/cm to about 10 mS/cm, preferably about 8 mS/cm. The concentration of the disodium hydrogen phosphate anhydrous is selected from about 0.01 M to about 1M, preferably 0.05 M. The second wash is performed at least one column volumes, preferably 3 column volumes, more preferably 6 column volumes or till absorbance is stabilized either of the above condition occurring first. The HIC column can then be eluted using an appropriate buffer. The elution buffer can be one or mixture of more than one buffer. The protein is eluted by a combination by giving a step gradient of 40% to 70% preferably 65% of second wash buffer and at least 75% and above of second wash buffer. The eluted protein is a third protein mixture which is collected in fractions. Artificial pool is prepared with the collected fractions. Artificial pool is analyzed to check the % of misfolded species by HI-HPLC and level of HCP by ELISA.

In certain embodiment, the eluted protein (third protein mixture) from hydrophobic interaction chromatography is optionally subjected to diafiltration via 30 kDa cutoff membrane against 20 mM Histidine hydrochloride, pH 5.5 buffer for six diafiltration volumes or till pH and conductivity of the retentate reaches less than 5.8 and 3.0 mS/cm, respectively.

In certain embodiment, the present invention also embodies the use of anion exchange Chromatography (HIC) process for purifying the TNFR:Fc fusion protein from mixture comprising protein of interest and HCP containing at least one protein degrading enzyme The third protein mixture obtained from HIC column and optionally after diafiltration can be subjected to an anion exchange chromatography column and the eluate obtained from anion exchange column can be referred as fourth protein mixture which have reduced level of HCP and protein degrading enzymes.

In one embodiment, the anion exchange chromatography is selected from DEAE sepharose fast flow, Fractogel® EMD DEAE (M), Toyopearl DEAE-650, Toyopearl DEAE-650.

In an embodiment the third protein mixture obtained from HIC column and optionally after diafiltration is subjected to an anion exchange chromatography column. Anion exchange is performed in bind-elute mode. The anion exchange column is equilibrated with a suitable buffer prior to sample loading. The suitable equilibration buffers are selected from histidine hydrochloride, phosphate, citrate, preferably histidine hydrochloride, at pH selected from about 4.5 to about pH 6, preferably pH 5.5; conductivity is selected from about 1 mS/cm to about 10 mS/cm, preferably 2 ms/cm. The concentration of histidine chloride is selected from 10 mM to 50 mM, preferably 20 mM. The third protein mixture is loaded onto the anion exchange column. The flow rate can be selected from at about 50 cm/hr to at about 300 cm/hr, preferably 150 cm/hr.

Following the loading of the anion exchange column, the column can be washed one or multiple times by using the equilibrating buffer or by employing different buffers. The anion exchange column is washed with the equilibration buffer for at least one column volumes, preferably 2 column volumes. This wash can optionally be followed by one or more wash. In preferred embodiment, anion exchange column is washed with the equilibration buffer for at least one column volumes, preferably 2 column volumes and then followed by an second wash buffer which comprises buffer selected from sodium acetate and at pH selected from about 4.5 to about pH 6, preferably pH 5.5, conductivity is selected from 1 mS/cm to about 20 mS/cm, preferably 8.2 ms/cm. The concentration of the sodium acetate is selected from about 50 mM to 125 mM, preferably 100 mM anion exchange column is washed with the equilibration buffer for at least one column volumes, preferably 3 column volumes, more preferably 6 column volumes, most preferably 8 column volumes.

The anion exchange column can then be eluted using an appropriate buffer. The elution buffer can be one or mixture of more than one buffer. The elution buffer comprises buffer selected from sodium acetate and at pH selected from about 4.5 to about pH 6, preferably pH 5.5, conductivity is selected from 10 mS/cm to about 30 mS/cm, preferably 15 ms/cm. The elute is collected and can be referred as fourth protein mixture.

In preferred embodiment, the present invention embodies the use of mixed mode chromatography (MMC) process for purifying the TNFR:Fc fusion protein from mixture comprising protein of interest and HCP containing at least one protein degrading enzyme.

The fourth protein mixture obtained from anion column can be subjected to a mixed mode chromatography column and the eluate obtained from mixed mode chromatography column can be referred as fifth protein mixture which has reduced level of HCP and protein degrading enzymes. The elute (fifth protein mixture) is substantially free of at least one of the protein degrading enzyme.

Mixed-mode chromatography column comprises both ligands containing positively charge moiety and hydrophobic moiety wherein the positively charge moiety has anion exchange (IEC) properties and hydrophobic moiety has hydrophobic interaction chromatography (HIC) properties. IEC/HIC mixed mode chromatography has improved separation power and selectivity on the grounds that it applies both electrostatic and hydrophobic interactions. Mixed mode chromatography can be performed using the combination of either anion exchange chromatography and HIC or cation exchange chromatography and HIC. Mixed-mode chromatography column can be selected from Capto adhere (N-Benzyl-N-methyl ethanol amine as ligand), Capto MMC (MMC ligand), MEP Hypercel (4-marcaptomethyl pyridine as ligand), HEA Hypercel (hexyl amine as ligand), PPA Hypercel (phenylpropylamine as ligand) exhibit many functionalities for interaction. These resins exhibit multiple functionalities for interaction. The most pronounced are ionic interaction, hydrogen bonding and hydrophobic interaction.

In an embodiment the fifth protein mixture obtained from anion exchange chromatography column is subjected to mixed-mode chromatography column. Mixed-mode chromatography is performed in the flow-through mode. Prior to loading, pH of the fifth protein mixture (sample) is adjusted to pH selected from about pH 6 to pH 7, preferably 6.5. The pH can be adjusted by using tris base having concentration from about 1M to 5M, preferably 2M. The conductivity of the sample is adjusted from about 30 mS/cm to about 42 mS/cm, preferably 35 ms/cm by the use of 2M-8M stock solution of sodium chloride. The mixed-mode column is equilibrated with a suitable buffer prior to sample loading. The suitable equilibration buffers are selected from histidine hydrochloride, phosphate, citrate preferably histidine hydrochloride containing sodium acetate, NaCl at pH selected from about 6 to about pH 7, preferably pH 7, conductivity is selected from about 30 mS/cm to about 42 mS/cm, preferably 35 ms/cm. The concentration of histidine chloride is selected from 10 mM to 50 mM, preferably 20 mM. The concentration of sodium acetate is selected from 180 mM to 300 mM, preferably 254 mM. Concentration of NaCl is selected from 180 mM to 300 mM, preferably 240 mM. The fifth protein mixture is loaded onto the Mixed-mode chromatography column. The flow rate can be selected from at about 20 cm/hr to at about 100 cm/hr, preferably 50 cm/hr and the protein is collected in fractions in the flow through (FT) mode. The elute fractions contains substantially pure protein of interest whereas the process and product related impurities are effectively bound to the column. Artificial pool is prepared with the collected FT fractions.

Artificial pool is analyzed to check the % of misfolded species by HI-HPLC and level of HCP by ELISA.

In an embodiment the elute obtained from the mixed-mode chromatography column can be subjected to virus filtration. Virus filtration is performed by using MMC FT is with PALL DV20 filter at 2-2.5 bar pressure.

In an embodiment, the protein obtained from the mixed-mode chromatography is concentrated by using tangential flow filtration (TFF). TFF can be Millipore Biomax 30 kDa membrane which is used for buffer exchange into formulation buffer followed and followed by protein of interest is concentrated in suitable concentration.

In one embodiment the invention is related to the process for purifying the TNFR:Fc fusion protein from the protein mixture by using mixed-mode chromatography column which can be performed at any step after affinity chromatography column.

In an embodiment the invention is related to the process for purifying the protein from the protein mixture comprising TNFR:Fc fusion protein and HCP impurities, the said process comprising:

a) obtaining protein mixture from the suitable mammalian expression system comprising TNFR:Fc fusion protein and host cell protein (HCP) impurities containing at least one protein degrading enzyme;

b) applying the protein mixture to affinity chromatography column;

c) eluting the TNFR:Fc fusion protein from affinity chromatography column wherein the eluted TNFR:Fc fusion protein is present in second protein mixture contains reduced amount of HCP impurity;

d) applying the second protein mixture to mixed-mode chromatography column;

e) eluting the TNFR:Fc fusion protein from a mixed-mode chromatography column wherein the eluted TNFR:Fc fusion protein is substantially free of HCP impurities containing at least one of the protein degrading enzyme.

In another embodiment the invention is related to the process for purifying the TNFR:Fc fusion protein from the protein mixture comprising TNFR:Fc fusion protein and at least one HCP impurity containing protein degrading enzyme, the said process comprising:

a) obtaining protein mixture from the suitable mammalian expression system comprising TNFR:Fc fusion protein and host cell protein (HCP) impurities containing at least one protein degrading enzyme;

b) applying the protein mixture to affinity chromatography column;

c) eluting the TNFR:Fc fusion protein from affinity chromatography column wherein the eluted TNFR:Fc fusion protein is present in second protein mixture contains reduced amount of HCP impurity;

d) applying the second protein mixture to Hydrophobic interaction chromatography column;

e) eluting the TNFR:Fc fusion protein from a Hydrophobic interaction chromatography column wherein the eluted protein of interest is present in third protein mixture contains reduced amount of HCP impurity;

f) applying the third protein mixture to mixed-mode chromatography column;

g) eluting the TNFR:Fc fusion protein from a mixed-mode chromatography column wherein the eluted protein of interest is substantially free of HCP impurity containing at least one of the protein degrading enzyme.

In another embodiment the invention is related to the process for purifying the protein from the protein mixture comprising TNFR:Fc fusion protein and at least one HCP impurity containing protein degrading enzyme, the said process comprising:

a) obtaining protein mixture from the suitable mammalian expression system comprising TNFR:Fc fusion protein and host cell protein (HCP) impurities containing at least one protein degrading enzyme;

b) applying the protein mixture to affinity chromatography column;

c) eluting the TNFR:Fc fusion protein from affinity chromatography column wherein the eluted TNFR:Fc fusion protein is present in second protein mixture contains reduced amount of HCP impurity;

d) applying the second protein mixture to Hydrophobic interaction chromatography column;

e) eluting the TNFR:Fc fusion protein from a Hydrophobic interaction chromatography column wherein the eluted TNFR:Fc fusion protein is present in third protein mixture contains reduced amount of HCP impurity;

f) applying the third protein mixture to anion exchange chromatography column;

g) eluting the TNFR:Fc fusion protein from a anion exchange chromatography column wherein the eluted protein of interest is present in fourth protein mixture contains reduced amount of HCP impurity;

h) applying the fourth protein mixture to mixed-mode chromatography column;

i) eluting the TNFR:Fc fusion protein from a mixed-mode chromatography column wherein the eluted TNFR:Fc fusion protein is substantially free of HCP impurity containing at least one of the protein degrading enzyme.

In another embodiment the invention is related to the process for purifying the TNFR:Fc fusion protein from the protein mixture comprising TNFR:Fc fusion protein and at HCP impurities the said process comprising:

a) obtaining protein mixture from the suitable mammalian expression system comprising fusion and host cell protein (HCP) impurities containing at least one protein degrading enzyme;

b) applying the protein mixture to affinity chromatography column;

c) applying more than one wash to affinity chromatography column;

c) eluting the TNFR:Fc fusion protein from affinity chromatography column wherein the eluted TNFR:Fc fusion protein contains reduced amount of HCP impurities comparatively performed the said process without applying more than one wash to affinity chromatography column.

In the embodiment, the purification of TNFR:Fc fusion protein comprises Protein A chromatography in the bind-elute mode, followed by Hydrophobic interaction chromatography in the bind-elute mode, followed by anion exchange chromatography in the bind-elute mode and followed by the Mixed-mode chromatography in the flow-through mode.

In the embodiment, ion exchange chromatography (IEC) and HIC conditions are the closest to physiological conditions which are fit for maintaining biological activity, the combinations of them are widely used in the separation of biological products. Mixed-mode chromatography column comprises both ligands containing positively charge moiety and hydrophobic moiety wherein the positively charge moiety has anion exchange (IEC) properties and hydrophobic moiety has hydrophobic interaction chromatography (HIC) properties. IEC/HIC mixed mode chromatography has improved separation power and selectivity on the grounds that it applies both electrostatic and hydrophobic interactions. Mixed mode chromatography can be performed using the combination of either anion exchange chromatography and HIC or cation exchange chromatography and HIC. Mixed-mode chromatography step can be carried out in the flow-through mode using commercially available resins such as Capto adhere (N-Benzyl-N-methyl ethanol amine as ligand), Capto MMC (MMC ligand), MEP Hypercel (4-marcaptomethyl pyridine as ligand), HEA Hypercel (hexyl amine as ligand), PPA Hypercel (phenylpropylamine as ligand) exhibit many functionalities for interaction. These resins exhibit multiple functionalities for interaction. The most pronounced are ionic interaction, hydrogen bonding and hydrophobic interaction.

Removal of HCP containing at least one of the protein degrading enzyme and other impurities comprising leached Protein A, aggregates, fragments, endotoxins, nucleic acids and viruses from monoclonal antibodies and TNFR:Fc fusion proteins is performed using Mixed-mode chromatography in the flow-through mode where the Protein-of-interest pass directly through the column while the contaminants/impurities are adsorbed. These contaminants/impurities also include misfolded forms of the Protein-of-interest due to their difference in the hydrophobicity from that of the Protein-of-interest.

Alternate method was tried to remove HCP, i.e., gelatin sepharose instead of mixed mode chromatography but it is not regulatory approved at the time of the invention.

In an embodiment, residual HCP levels were detected using the more sensitive Gelatin zymography. Gelatin zymography offers a much higher sensitivity in detecting certain proteases (specifically matrix metalloprotease, more specifically gelatinases), which are one form of HCP that are secreted into the HCCF upon cell culture clarification. The presence of residual proteases in the intermediate purification stage material is evident from the positive gelatinase activity on the gelatin zymography. The commercial HCP detection kits or the process-specific HCP ELISA kits have lower sensitivity, usually above 1 PPM of HCP. However, the Gelatin zymography also has limitations and can only detect proteolytic activity above 0.1 PPM level in the intermediate purification stage material or in the purified Protein-of-interest.

In another embodiment, residual protease activity was detected in HCCF and post-Protein A chromatography from various CHO cell lines expressing Protein-of-interest as observed by Gelatin zymography.

Figure 3:
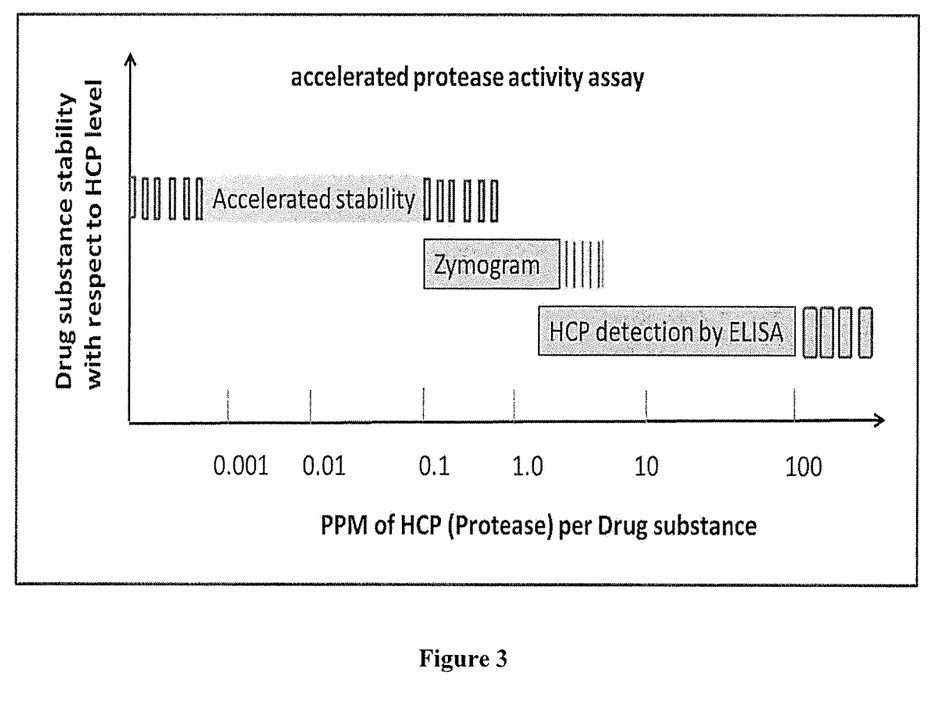
FIG. 3 illustrate comparison of sensitivity of Accelerated stability study verses Zymogram and ELISA in the detection of HCP.

In another embodiment, a more sensitive test for the residual HCP, in terms of protease activity, was introduced for intermediate purification steps by conducting Accelerated Degradation study using a Marker protein at incubation temperature>2° C. (FIG. 3).

In another embodiment the invention substantially reduced the HCP impurities containing at least one protein degrading enzyme by at least 90% preferably by at least 99% and more preferably reduced to the extent to meet acceptable limit.

In another embodiment the invention substantially reduced the HCP impurities containing at least one protein degrading enzyme and stabilizes the TNFR:Fc fusion protein by at least two weeks, preferably by at least one month, more preferably by at least 6 month and most preferably by at least one year.

The examples which follow are illustrative of the invention and are not intended to be limiting.

Experimental Section

Etanercept was used as a model TNFR:Fc fusion protein as an example of marker protein. Etanercept was produced by mammalian cell culture using CHO cells genetically engineered by the recombinant DNA technology. The CHO cells were cultured in a fed-batch process. Etanercept was derived from different production batches which were used in the examples. The efficiency of the removal of proteases was evaluated by gelatin zymography and Accelerated Degradation study of a marker protein.

Example 1

Etanercept Purification by using Protein A Chromatography

The clarified harvested cell culture fluid (HCCF) was pre-conditioned by adjusting the pH to 8.2-9.2. The pre-conditioned HCCF was loaded onto a protein A chromatography (MabSelect Sure LX, GE Healthcare). The column was pre-equilibrated with equilibration buffer (50 mM Tris-Cl buffer). Intermediate washes were carried out by wash buffer 1 (50 mM Tris, 1.5 M urea, 1.5% tween 80 and 7.5% isopropanol, 1 M NaCl and 5 mM EDTA, pH 8.5) and wash buffer 2 (50 mM trisodium citrate dehydrate buffer, pH 4.5) and finally Etanercept was eluted in 50 mM trisodium citrate dehydrate buffer, pH 3.5.

Example 2

Etanercept Purification by using Protein A Chromatography

The 0.2 micron filtered clarified harvest cell culture fluid (HCCF) is and then pH adjusted to 8.5±0.2 with 2 M Tris base just before loading onto the affinity column. The pH adjusted solution is loaded at 100 cm/hr onto Protein A (MabSelect Sure LX, GE Healthcare) column with a bed height of 20 cm (dynamic binding capacity: Not more than 17 mg of etanercept per ml of resin), pre-equilibrated with equilibration buffer (50 mM Tris-Cl buffer, containing 150 mM NaCl, and 5 mM EDTA, pH 8.5, conductivity: 18±2 mS/cm) for two column volumes. Once the load is over, the column is first washed with the equilibration buffer for 2 column volumes, followed by an intermediate wash A buffer (50 mM Tris, 1.5 M urea, 1.5% tween 80 and 7.5% isopropanol, 1 M NaCl and 5 mM EDTA pH 8.5, conductivity: 65±5 mS/cm) for 6 column volumes followed by intermediate wash B buffer (50 mM trisodium citrate dihydrate, pH 4.5, conductivity: 12±2 mS/cm) for 1 column volumes which is again followed by a final intermediate wash C buffer (10% buffer B against intermediate wash 2 buffer) for 1 CV. Finally, etanercept is eluted by a combination of linear (10-90% elution buffer for 6 CV) and step gradient (elution buffer: 50 mM trisodium citrate dihydrate pH 3.0 and conductivity: 13±2 mS/cm). The elution is collected in fractions. The collected fractions are used for low pH treatment. The pooling is performed such that oxidized species and HCP is reduced by at least 10% of the protein mixture.

Example 3

Mixed-Mode Chromatography for Purification of Etanercept

The eluted protein solution from anion exchange chromatography is pH adjusted to 6.5 with 2 M Tris base. The conductivity of the solution is adjusted to 35 mS/cm with 4 M NaCl stock solution. Mixed mode chromatography is performed on Capto Adhere resin (GE Healthcare) in a negative binding mode with a bed height of 18 cm. The column is equilibrated with 20 mM Histidine Hydrochloride, 240 mM sodium acetate and 220 mM NaCl, pH 6.5, conductivity: 35±2 mS/cm). The protein solution is loaded onto the column at a flow rate of 50 cm/hr and the flow through (FT) is collected in fractions as this contains pure Etanercept whereas the process and product related impurities are effectively bound to the column. Artificial pool is prepared with the collected FT fractions. Artificial pool is analyzed to check the % of misfolded species by HI-HPLC and level of HCP by ELISA. Based on the analysis report the pooling the pooling is performed such that misfolded species and HCP is reduced by at least 10% of the protein mixture.

Example 4

Etanercept Purification from Protein A Chromatography without using Mixed-Mode

Figure 1:
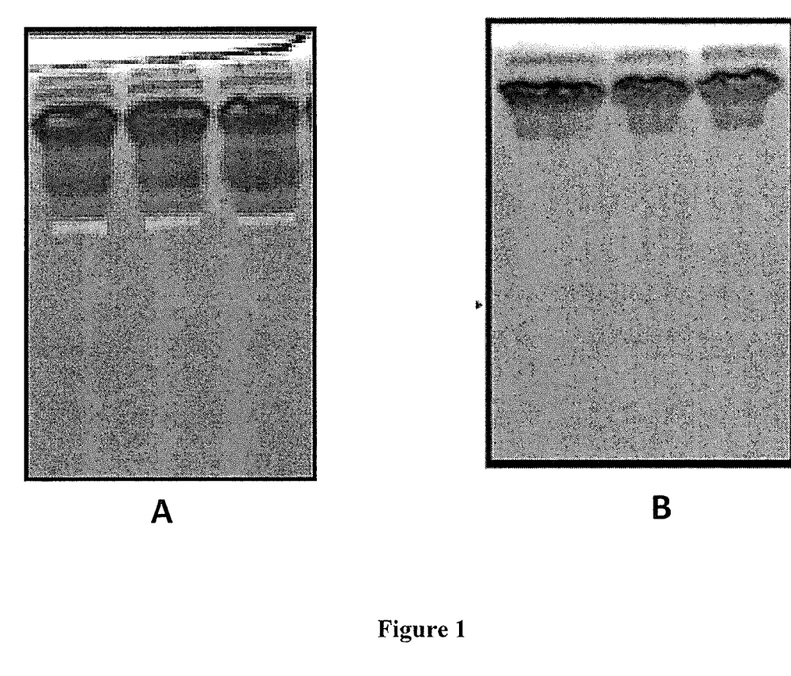
FIG. 1(A) illustrates Gelatin zymograms showing protease activity present in protein A eluates without intermediate wash steps in Protein A chromatography.
FIG. 1(B) illustrates Gelatin zymograms showing protease activity absent in protein A eluates with intermediate wash steps in Protein A chromatography.

The protein A chromatography was performed without the intermediate washes. It was observed that protein A chromatography cleared a large proportion of HCP, but some amount of HCP was still co-eluted with Etanercept as inferred from the positive gelatinase activity in the protein A eluate as evident from the observed bands on gelatin zymogram as shown in FIG. 1A.

The protein mixture (Second protein mixture) obtained from Protein A column was further purified with HIC column chromatography. Load preparation is done with gradually adding the high salt buffer (0.05 M disodium hydrogen phosphate anhydrous, 0.8 M Trisodium citrate dihydrate, pH 6.5, conductivity: 65±5 mS/cm) to the protein solution to obtain a conductivity of 50±2 mS/cm. Hydrophobic interaction chromatography is performed on Butyl Toyopearl 650 M resin at a bed height of 25±2 cm. The column is equilibrated with equilibration buffer (High salt buffer diluted with WFI such that conductivity is 50±2 mS/cm). The protein sample is loaded onto the column at a flow rate of 150 cm/hr and post loading; the column is washed with the equilibration buffer for 1.5 column volumes. The column is washed with 25% of buffer B (buffer B: 0.05 M disodium hydrogen phosphate anhydrous, pH 6.5, conductivity: 8±1 mS/cm) for 6 column volumes or till absorbance is stabilized either of the above condition occurring first. The target protein is eluted from the column by giving a step gradient of 65% B. The eluted protein (third protein mixture) is collected in fractions. Artificial pool is prepared with the collected fractions. Artificial pool is analyzed to check the % of misfolded species by HI-HPLC and level of HCP by ELISA.

The eluted protein from hydrophobic interaction chromatography is subjected to diafiltration via 30 kDa cutoff membrane against 20 mM Histidine hydrochloride, pH 5.5 buffer for six diafiltration volumes or till pH and conductivity of the retentate reaches less than 5.8 and 3.0 mS/cm, respectively. Thereafter the eluted protein is further purified by using anion exchange chromatography.

Anion exchange chromatography is performed on DEAE Sepharose fast flow at a bed height of 25 cm. The column is equilibrated with equilibration buffer (20 mM Histidine hydrochloride, pH 5.5, conductivity: 2±1 mS/cm). The buffer exchanged protein solution is loaded onto the column at a flow rate of 150 cm/hr and the column is washed with equilibration buffer for 2 column volumes. The column is further washed with intermediate wash buffer (equilibration buffer containing 100 mM sodium acetate, pH 5.5, conductivity: 8.2±1 mS/cm) for 8 column volumes. The target protein is finally eluted (Fourth protein mixture) with elution buffer (Equilibration buffer containing 240 mM sodium acetate, pH 5.5, conductivity: 15±2 mS/cm).

Example 5

Etanercept Purification using Multiple Column Chromatographies using Mixed-Mode

Protein A column chromatography was performed as described in the example 1 or example 2 of the present invention. This helped in separating the tightly bound Etanercept from HCP. Gelatin zymography did not show any gelatinase activity when Protein A eluate was analyzed as shown in FIG. 1B. However, presence of trace amounts of HCP (protease) in the Protein A eluate was evident only from the Accelerated Degradation study of a marker protein. The data shown in Table 1A (Example 4) shows the extent of degradation (17% at 2-8° C. and 51% at 25° C.) of the marker protein upon accelerated study. The protein mixture (Second protein mixture) obtained from Protein A column was further purified with HIC column chromatography. Load preparation is done with gradually adding the high salt buffer (0.05 M disodium hydrogen phosphate anhydrous, 0.8 M Trisodium citrate dihydrate, pH 6.5, conductivity: 65±5 mS/cm) to the protein solution to obtain a conductivity of 50±2 mS/cm. Hydrophobic interaction chromatography is performed on Butyl Toyopearl 650 M resin at a bed height of 25±2 cm. The column is equilibrated with equilibration buffer (High salt buffer diluted with WFI such that conductivity is 50±2 mS/cm). The protein sample is loaded onto the column at a flow rate of 150 cm/hr and post loading; the column is washed with the equilibration buffer for 1.5 column volumes. The column is washed with 25% of buffer B (buffer B: 0.05 M disodium hydrogen phosphate anhydrous, pH 6.5, conductivity: 8±1 mS/cm) for 6 column volumes or till absorbance is stabilized either of the above condition occurring first. The target protein is eluted from the column by giving a step gradient of more than 45%, preferably 65% B. The eluted protein (third protein mixture) is collected in fractions. Artificial pool is prepared with the collected fractions. Artificial pool is analyzed to check the % of misfolded species by HI-HPLC and level of HCP by ELISA. Based on the analysis report the pooling is performed such that misfolded species and HCP is reduced by at least 10% of the second protein mixture.

Anion exchange chromatography is performed on DEAE Sepharose fast flow at a bed height of 25 cm. The column is equilibrated with equilibration buffer (20 mM Histidine hydrochloride, pH 5.5, conductivity: 2±1 mS/cm). The third protein mixture is loaded onto the column and washed with equilibration buffer. The column is further washed with intermediate wash buffer (equilibration buffer containing 100 mM sodium acetate, pH 5.5, conductivity: 8.2±1 mS/cm). The target protein is finally eluted (Fourth protein mixture) with elution buffer (Equilibration buffer containing 240 mM sodium acetate, pH 5.5, conductivity: 15±2 mS/cm).

Fourth eluted protein mixture is further purified by the Mixed-mode chromatography as described in example 2. The accelerated degradation study is shown in Table 1B and FIG. 2B.

TABLE 1

SEC-HPLC analysis of marker protein for Accelerated degradation study:

| A (Example 4) | | | | B (Example 5) | | | |
|---|---|---|---|---|---|---|---|
| Time point | % HMW | % Monomer | % LMW | Time point | % HMW | % Monomer | % LMW |
| Zero time | 2.54 | 97.46 | — | Zero time | 0.98 | 99.02 | — |
| 2-8° C. 2 Weeks | 2.54 | 80.26 | 17.2 | 2-8° C. 2 Weeks | 0.98 | 99.02 | — |
| 25° C. 2 Weeks | 3.41 | 45.32 | 51.26 | 25° C. 2 Weeks | 0.98 | 99.02 | — |
| 40° C. 2 Weeks | 58.47 | 7.7 | 33.82 | 40° C. 2 Weeks | 1.48 | 98.52 | — |

Mixed-mode chromatography further helped in removing this trace amount of proteases which is indicative of much higher HCP removal (more specifically protease removal) by this step. Table 1B (Example 5) shows no degradation of the marker protein in Accelerated Degradation study after incubation for two weeks.

TABLE 2 shows the purity profile at different steps

| Stage | HI-HPLC Analysis (%) | | | SEC-HPLC Analysis (%) | | | HCP (PPM) |
|---|---|---|---|---|---|---|---|
| | Degraded Form | Proper Form | Misfolded form | HMW (High molecular weight) | Monomer | LMW (Low molecular weight) | |
| Affinity Load | 5.1 | 44 | 50.8 | 6.49 | 80.97 | 12.54 | 334184 |
| Affinity Elution | 1.3 | 43.7 | 55 | 11.61 | 87.95 | 0.44 | 233 |
| HIC load | 1.4 | 42.8 | 55.8 | 10.57 | 89.35 | 0.08 | ND* |
| HIC Elution | 1.3 | 72.8 | 25.8 | 1.56 | 97.95 | 0.48 | 135 |
| AEX Load | 1.4 | 73 | 25.6 | 1.61 | 97.83 | 0.5 | ND* |
| AEX Elution | 1.4 | 66.2 | 32.5 | 2.22 | 97.31 | 0.47 | ND* |
| MMC Load | 1.5 | 65.1 | 33.4 | 2.25 | 96.87 | 0.88 | 96 |
| MMC FT | 0.6 | 88.4 | 11 | 0.84 | 99.16 | 0 | 32 |

ND—Not determined

Example 6

Figure 2A:
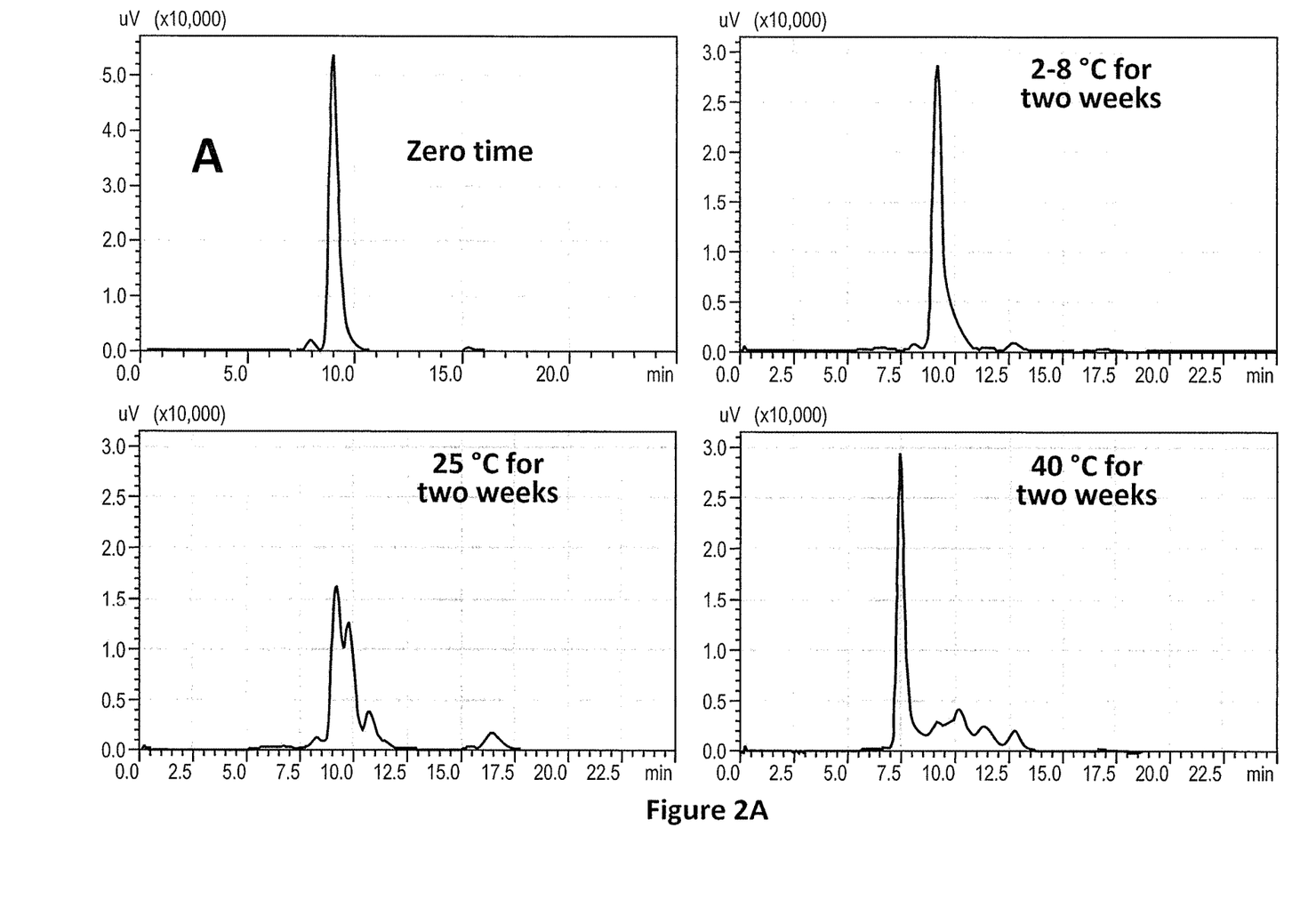
FIG. 2(A) illustrates accelerated protease degradation study analysis by Size Exclusion-HPLC of downstream purification without mixed mode chromatography as polishing step.
Figure 2B:
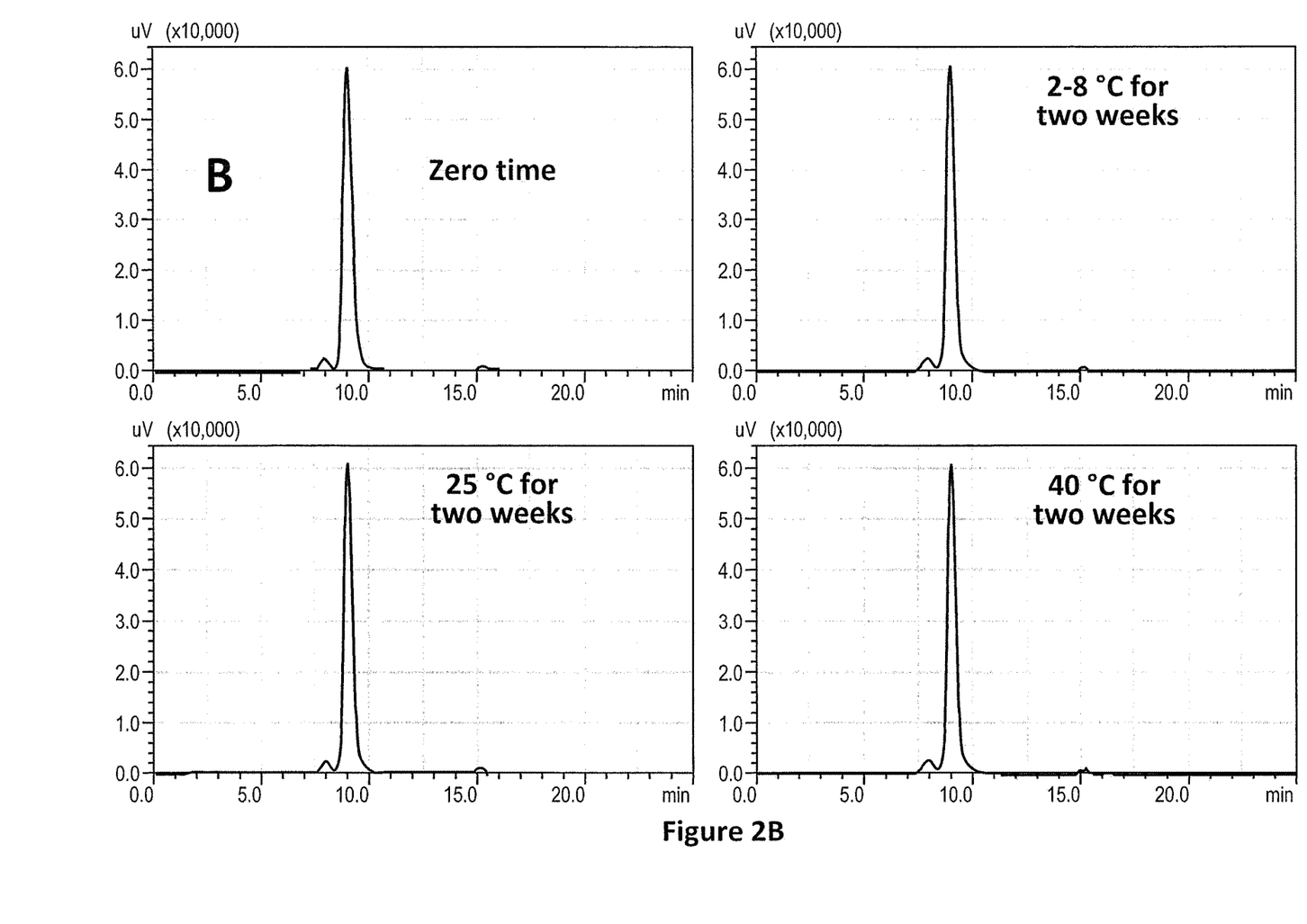
FIG. 2(B) illustrates accelerated protease degradation study analysis by Size Exclusion-HPLC of downstream purification with Mixed-mode chromatography.

Accelerated Degradation study of a marker protein was performed on Etanercept purified from Example 4 and Example 5 by HPLC or any appropriate detection tool. The samples from both the experiments were subjected to Accelerated Degradation study for a period sufficient to show degradation usually within 2 weeks and the digestion of the marker protein was analysed by HPLC or any appropriate detection tool. It was observed that Etanercept purified from example 5 showed no degradation of the marker protein as shown in FIG. 2B as compared to that from Example 4 as shown in FIG. 2A, indicating that the purification scheme described in Example 5 gives higher degree of HCP removal, preferably in terms of protease removal, even more preferably of gelatinase removal.

From the above examples it can be concluded that Mixed-mode chromatography offers an excellent intermediate purification and/or polishing step for monoclonal antibodies and TNFR:Fc fusion proteins by removing trace amounts of HCPs which otherwise would be present along with the Protein-of-interest using conventional chromatographic processes that does not use Mixed-mode chromatography. The latter step offers a robust chromatography platform for the purification of monoclonal antibodies and TNFR:Fc fusion proteins. The ligands used in such resins, for example N-Benzyl-N-methyl ethanol amine, 4-marcaptomethyl pyridine, hexyl amine, phenylpropylamine exhibit many functionalities for binding of host proteins.

Gelatin Zymography:

Zymography is known as an electrophoretic technique, commonly based on sodium dodecyl sulfate-polyacrylamide gel electrophoresis (SDS-PAGE), which contains gelatin as substrate copolymerized within the polyacrylamide gel matrix, for the detection of protease activity or gelatinase activity. Samples are normally prepared by the standard SDS-PAGE treatment buffer, under non-reducing conditions, i.e. absence of heating and reducing agent [2-mercaptoethanol, dithiothreitol (DTT)]. After the electrophoretic run, the SDS is soaked out from the gel (zymogram) by incubation in a non-buffered Triton X-100, followed by incubation in an appropriate activation buffer, for an optimized length of time and temperature, depending on the type of enzyme being assayed and the type of substrate being degraded. The zymogram is subsequently coomassie stained, and areas of digestion are distinguished by a zone of clearance in the blue background. For the specific case of proteases (gelatinases) gelatin is one of the most frequently used substrate. In this case, visualization of the proteolytic activity appears as clear bands over a deep blue background, after Coomassie staining.

Accelerated Degradation Study:

Accelerated degradation study was performed by incubating the purified marker protein at 2-8° C., 25° C. and 40° C. for a period of two weeks. Post incubation, protein samples were analyzed by SE-HPLC to detect appearance of LMW species upon marker protein degradation.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof.

The invention claimed is:

1. A process for purifying the TNFR:Fc fusion protein from the protein mixture comprising TNFR:Fc fusion protein and at least one HCP impurity containing protein degrading enzyme, the said process comprising:
   a) obtaining protein mixture from the suitable mammalian expression system comprising TNFR:Fc fusion protein and host cell protein (HCP) impurities containing at least one protein degrading enzyme;
   b) applying the protein mixture to Protein A affinity chromatography column;
   c) eluting the TNFR:Fc fusion protein from Protein A affinity chromatography column wherein the eluted TNFR:Fc fusion protein is present in second protein mixture containing reduced amount of HCP impurity;
   d) applying the second protein mixture to Hydrophobic interaction chromatography column;
   e) eluting the TNFR:Fc fusion protein from a Hydrophobic interaction chromatography column wherein the eluted TNFR:Fc fusion protein is present in third protein mixture contains reduced amount of HCP impurity;

f) applying the third protein mixture to anion exchange chromatography column;

g) eluting the TNFR:Fc fusion protein from a anion exchange chromatography column wherein the eluted protein of interest is present in fourth protein mixture containing reduced amount of HCP impurity;

h) applying the fourth protein mixture to mixed-mode chromatography column;

i) eluting the TNFR:Fc fusion protein from a mixed-mode chromatography column wherein the eluted TNFR:Fc fusion protein is substantially free of HCP impurity containing at least one of the protein degrading enzyme.

2. The process as claimed in claim 1, wherein the mixed-mode chromatography comprises anion exchange and hydrophobic interaction chromatography.

3. The process as claimed in claim 2, wherein the mixed-mode chromatography is performed in flow-through mode.

4. The process as claimed in claim 3, wherein the mixed-mode chromatography column is selected from Capto adhere (N-Benzyl-N-methyl ethanol amine), Capto MMC (MMC ligand), MEP Hypercel (4-marcaptomethyl pyridine), BEA Hypercel (hexylamine) and PPA Hypercel (phenylpropylamine).

5. The process as claimed in claim 4, wherein the mixed-mode chromatography column is Capto adhere (N-Benzyl-N-methyl ethanol amine).

6. The process as claimed in claim 1, wherein the protein mixture is applied on to the mixed-mode chromatography column in step (h) at a suitable pH in the range of about pH 6 to about pH 6.8.

7. The process as claimed in step (h) of claim 1, wherein the protein mixture is applied on to the mixed-mode chromatography column at a suitable conductivity in the range of about 30 mS/cm to about 42 mS/cm.

8. The process as claimed in step (h) of claim 1, wherein the mixed-mode column is equilibrated with a buffer comprising 20 mM histidine hydrochloride, 240 mM sodium acetate and 220 mM NaCl.

9. The process as claimed in claim 1, wherein the eluted TNFR:Fc fusion protein in step (i) is ~≥80% pure.

10. The process as claimed in claim 1, wherein the TNFR:Fc fusion protein is Etanercept.

11. The process as claimed in step (b) of claim 1, wherein the Protein A column is pre-equilibrated with an equilibration buffer comprising about 50 mM Tris-Cl at pH 8.5 and 18 mS/cm conductivity.

12. The process as claimed in claim 1, wherein the step (b) further comprises:

a') washing the bound TNFR:Fc fusion protein with a buffer having a pH in the range of about pH 8 to about pH 9 and/or b') washing the bound TNFR:Fc fusion protein with a buffer having a pH in the range of about pH 4 to about pH 5.

13. The process as claimed in claim 12 wherein the step (a') comprises a buffer selected from Tris chloride, HEPES, Triethanolamine, Borate and Glycine-NaOH.

14. The process as claimed in step (c) of claim 1, wherein the TNFR:Fc fusion protein is eluted with a linear gradient or a step gradient or a combination thereof.

15. The process as claimed in claim 14, wherein the TNFR:Fc fusion protein is eluted with a combination of linear gradient and step gradient.

16. The process as claimed in claim 15, wherein the linear gradient is achieved by mixing an elution buffer having a pH in the range of about 2 to about 3.5 and a wash buffer having a pH in the range of about 4 to 5 in a suitable ratio.

17. The process as claimed in claim 1, wherein the protein degrading enzyme is removed by at least 90%.

18. The process as claimed in claim 1, wherein the HCP impurities are selected from aggregates, misfolded protein, fragments, endotoxins, nucleic acids, viruses and proteases.

19. The process as claimed in claim 1, wherein the hydrophobic interaction chromatography column is selected from Butyl Toyopearl 650 M resin, Toyopearl Phenyl-650, Butyl Sepharose 6 Fast Flow and Phenyl Sepharose 6 Fast Flow.

20. The process as claimed in claim 1, wherein the anion exchange chromatography column is selected from Quaternary Ammonium, Sulfonic Acid, Diethylaminoethyl and Carboxymethyl.

* * * * *